United States Patent
Shimizu

(10) Patent No.: US 6,679,908 B2
(45) Date of Patent: Jan. 20, 2004

(54) FACIAL TREATMENT DEVICE

(75) Inventor: Hirohisa Shimizu, Osaka (JP)

(73) Assignee: Oohiro Works, Ltd., Osaka (JP)

( * ) Notice: Subject to any disclaimer, the term of this patent is extended or adjusted under 35 U.S.C. 154(b) by 15 days.

(21) Appl. No.: 09/752,341

(22) Filed: Dec. 29, 2000

(65) Prior Publication Data

US 2001/0007952 A1 Jul. 12, 2001

(30) Foreign Application Priority Data

Jan. 11, 2000 (JP) ........................................ 2000-002920

(51) Int. Cl.[7] .................................................. A61F 7/00
(52) U.S. Cl. ........................................ 607/109; 607/96
(58) Field of Search ................................ 607/96, 109

(56) References Cited

U.S. PATENT DOCUMENTS

| 5,097,828 A | * | 3/1992 | Deutsch | ........................ 607/104 |
| 5,209,227 A | * | 5/1993 | Deutsch | ........................ 607/104 |
| 5,327,886 A |   | 7/1994 | Chiu    |                                 |
| 6,023,932 A | * | 2/2000 | Johnston | ........................ 607/96 |

FOREIGN PATENT DOCUMENTS

TW          258921          10/1995

* cited by examiner

*Primary Examiner*—Gerald A. Michalsky
(74) *Attorney, Agent, or Firm*—Burr & Brown

(57) ABSTRACT

The present invention provides a facial treatment device which can repeat warming and cooling of the face of a person while the massages are given to the face at the same time, whereby the beauty effects such as the facial treatment and body slimming can be mutually and efficiently obtained. A Peltier element 12 is placed adjacent to a probe 11 having a high thermal conductivity, which can abut the face of a person 19 to be treated. Then, the current is supplied by a DC power supply 101 to the Peltier element 12 and the direction of the current can be switched between the forward and backward directions by the selector switch 100. Thereby, the cooling and warming of the probe 11 is repeated. At the same time, a motor 15 having an eccentric weight 17 attached thereto is driven, whereby the probe 11 is vibrated.

1 Claim, 4 Drawing Sheets

FACIAL TREATMENT DEVICE

FIELD OF THE INVENTION

The present invention relates to a facial treatment device which is used for business purposes in aesthetic salons or the like and, more particularly, to a facial treatment device which alternately warms and cools the face of a person to be treated.

BACKGROUND OF THE INVENTION

In recent years, various types of facial treatment devices have come into wide use with the growing aesthetic senses of women.

FIG. 3 is a diagram illustrating a structure of a prior art facial treatment device.

In this figure, reference numeral 30 denotes a facial treatment device body. Numeral 31 denotes a probe having a high thermal conductivity, which is attached to an opening of the body 30. Numeral 32 denotes a Peltier element which is placed adjacent to the probe 31 and cools or warms the probe 31. Numeral 33 denotes a radiating fin which is provided to widen the heating surface of the Peltier element. Numeral 34 denotes a blower fan which sends air and cools the radiating fin 33 which radiate the heat stored in the Peltier element. Numeral 35 denotes a cord which is attached to the body 30. Numeral 36 denotes a person to be treated.

As shown in FIG. 4, a double-pole double-throw selector switch 100 and a DC power supply 101 are connected to the Peltier element 32. When the selector switch 100 is switched to the side A, the voltage is applied by the DC power supply 101 in the direction of C. On the other hand, when the selector switch 100 is switched to the side B, the polarity of the voltage which is applied, by the DC power supply 101, to the Peltier element 32 is reversed. As the DC power supply 101, a stable switching power supply is employed in consideration of ripples or the like, and a rectifier circuit with a diode bridge is usually employed.

When the DC voltage in a prescribed direction is applied by the DC power supply 101, the Peltier element 32 absorbs the heat on one of the front and rear surfaces while radiating the heat from the other surface. When the direction of the current is switched to the reverse direction by the selector switch 100, the heat radiates from the surface which has absorbed the heat, while the surface from which the heat has radiated absorbs the heat.

Hereinafter, the description will be given of the operation of the so-constructed facial treatment device when the facial treatment is performed using this facial treatment device, with reference to FIGS. 3 and 4.

Initially, the probe 31 which has been cooled or heated by the Peltier element 32 is put on the face of the person 36 to be treated. When the probe 31 has been cooled, the heat is absorbed an the surface 32a of the Peltier element 32 on the side of the probe 31 while the heat radiates from the surface 32b on the opposite side via the radiating fin 33. When the selector switch 100 is switched by an external switch (nor shown) and the direction of the current supplied to the Peltier element 32 is switched, the heat radiates from the surface 32a of the Peltier element 32 which engages the probe 31 and the surface 32a heats the probe 31 while the surface 32b, on the opposite side absorbs the heat.

As described above, when the probe 31 which has been cooled or heated by the Peltier element 32 is put to the face of the person 36 to be treated and the external switch (not shown) is operated to switch the selector switch 100 every predetermined period, the probe 31 is repeatedly cooled or heated. Accordingly, warm and cold stimuli can be repeatedly given to the skin of the person 36, whereby the beauty effects such as tightening of the skin and improvement of blood circulation of the person 36 are obtained.

There are a variety of facial treatments which are usually executed in aesthetic salons and the like, and plural facial treatment devices for various purposes are used to obtain various beauty effects in a combined manner. In addition to the above-mentioned facial treatment device which executes the facial treatments utilizing the heating or cooling effects of the Peltier element, facial treatment devices utilizing steam, ultrasonics or the like are employed, for example.

However, since plural facial treatment devices are used in a series of facial treatment processes, it takes a long time to execute all the processes or it costs much to get the facial treatment devices for various purposes ready.

Further, there is no conventional facial treatment device which alternately warms and cools the skin of the person to be treated and has a vibration function.

SUMMARY OF THE INVENTION

It is an object of the present invention to provide a facial treatment device which gives massages to the skin of the person to be treated in addition to the stimuli given by the warming or cooling, thereby further increasing the beauty effects such as the facial treatments and body slimming as well as reducing the time required for the beauty treatments or achieving economy.

Other objects and advantages of the present invention will become apparent from the detailed description and specific embodiments described are provided only for illustration since various additions and modifications within the spirit and scope of the invention will be apparent to those of skill in the art from the detailed description.

A facial treatment device for giving beauty treatments to a face of a person to be treated according to a 1st aspect of the present invention comprises: a probe which has a high thermal conductivity and can abut the face of the person; a Peltier element which is placed adjacent to the probe; a current supply means for supplying current to the Peltier element; a current direction switching means for switching the direction of the current which is passed by the current supply means to the Peltier element between forward and backward directions; a radiating means for radiating heat which has been stored in the Peltier element; a blower fan for sending air to cool the radiating means; and a vibration generating means for vibrating the probe. Therefore, the face of the person to be treated can be alternately warmed and cooled while the massages are simultaneously given to the face, whereby the respective beauty treatment effects and relaxing effects can be obtained together. Besides, the plural kinds of beauty treatment effects are combined and obtained by one facial treatment device. Therefore, the processing time required for the beauty treatments can be reduced and the more economical facial treatments can be realized.

According to a 2nd aspect of the present invention, the facial treatment device of the 1st aspect comprises the vibration generating means comprising: a vibrating motor; and a weight which is eccentrically attached to the motor, and the vibration generating means vibrates the probe by driving the motor. Therefore, the face of the person to be treated can be alternately warmed or cooled while the massages are simultaneously given to the face, whereby the respective beauty treatment effects or relaxing effects can be obtained together. Besides, the plural kinds of beauty treatment effects are combined and executed by one facial treatment device. Therefore, the processing time required for the beauty treatments can be reduced and the more economical facial treatment processing can be realized.

According to a 3rd aspect of the present invention, the facial treatment device of the 1st aspect comprises: the vibration generating means comprising a weight which is eccentrically attached to a blade of the blower fan, and the vibration generating means vibrates the probe by driving the blower fan. Therefore, the face of the person to be treated can be alternately warmed or cooled while the massages are simultaneously given to the face, whereby the respective beauty treatment effects or relaxing effects can be obtained together. Besides, the plural beauty treatment effects are combined and executed by one facial treatment device. Therefore, the processing time required for the beauty treatments can be reduced and the more economical facial treatment processing can be realized.

DETAILED DESCRIPTION OF THE PREFERRED EMBODIMENTS

Embodiment 1

Figure 1:
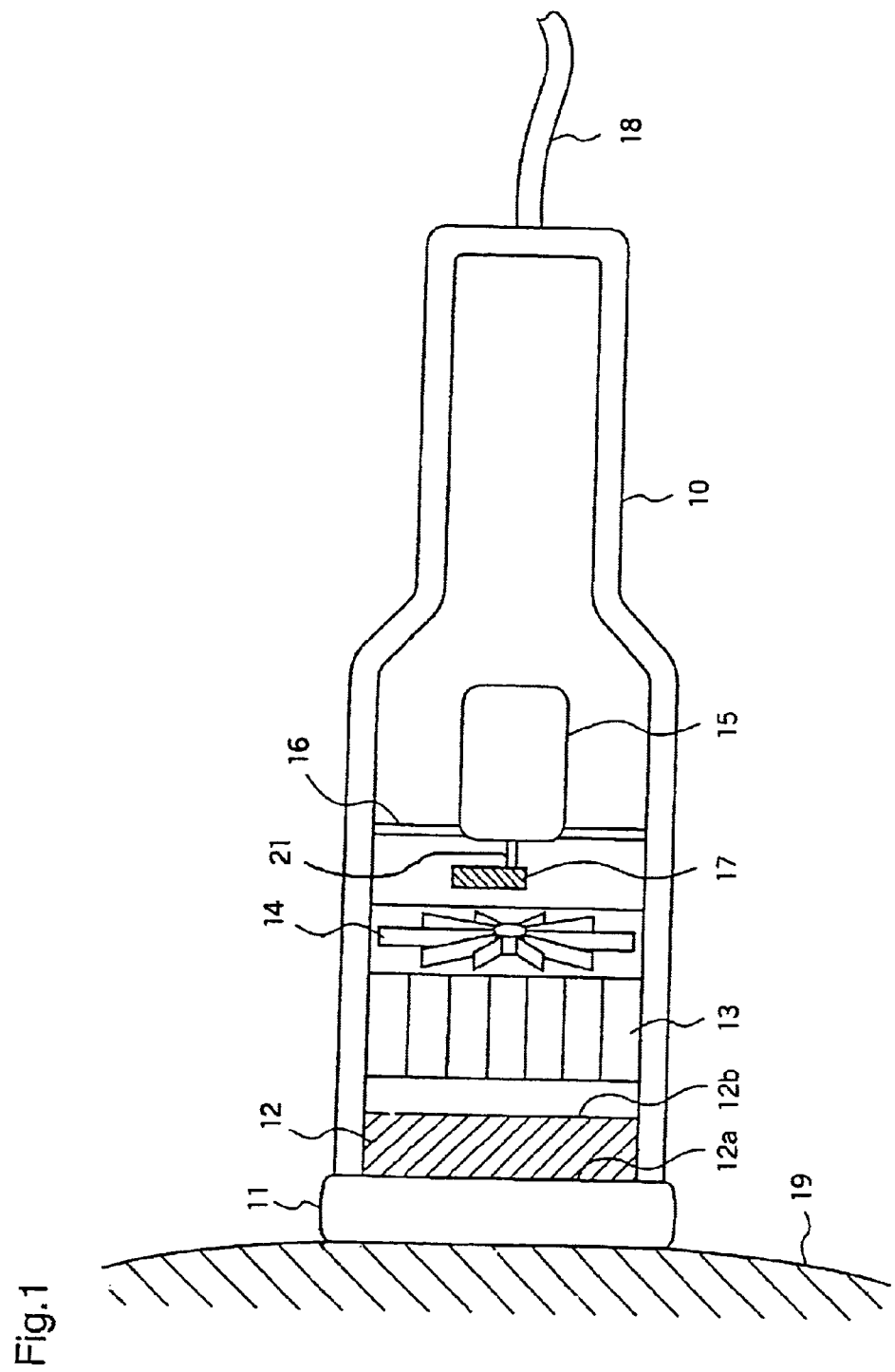
FIG. 1 is a diagram illustrating an example of a structure of a facial treatment device according to a first embodiment of the present invention.

FIG. 1 is a diagram illustrating an example of a structure of a facial treatment device according to a first embodiment of the present invention.

In this figure, reference numeral 10 denotes a facial treatment device body. Numeral 11 denotes a probe having a high thermal conductivity, which is attached to an opening of the body 10. Numeral 12 denotes a Peltier element which is placed adjacent to the probe 11 and heats or cools the probe 11. Numeral 13 denotes a radiating fin which is provided adjacent to the Peltier element 12 to widen the heating surface of the Peltier element 12. Numeral 14 denotes a blower fan for sending air to the radiating fin 13 which radiates the heat stored in the Peltier element 12 and cooling the radiating fin 13. Numeral 15 denotes a motor. Numeral 16 denotes a supporting axis for fixing the motor 15 to the body 10. Numeral 17 denotes a weight which is eccentrically attached to the motor 15. The motor 15 and the weight 17 constitute a vibration generating means, the motor having a shaft 21, the weight 17 being eccentrically directly attached to the shaft 21 of the motor 15, and the motor 15 being driven to vibrate the probe 11. Numeral 18 denotes a cord which is attached to the body 10. Numeral 19 denotes a person to be treated.

Hereinafter, the operation of the facial treatment device according to the first embodiment will be described with reference to FIGS. 1 to 4.

Similarly to the prior art facial treatment device, the DC voltage in a prescribed direction is applied by the DC power supply 101 to the Peltier element 12 which is provided adjacent to the probe having a high thermal conductivity. Then, the direction of the current is switched by the selector switch 100 every prescribed period. Accordingly, the probe 11 is repeatedly cooled or heated and the face of the person 19 to be treated can be warmed or cooled.

At this time, when the motor 15 is driven by a control switch (not shown), the motor 15 with the eccentric weight 17 is rotated and accordingly the body 10 and the probe 11 are vibrated. The vibrations of the probe 11 give facial massaging effects to the person 10.

When the stimulation by the warming or cooling is alternately given to the skin of the person 19 and the massages are simultaneously given to the person 19, the beauty effects of the facial treatment and slimming such as tightening of the skin, activation of the metabolism of the skin and removal of dirt in the pores can be further increased. Further, the vibration function has relaxing effects for gently massaging the skin and smoothing the nerves.

Besides, the skin is warmed or cooled while the massages are simultaneously given to the skin, and these two types of beauty treatments are executed together by one facial treatment device, whereby the processing time which is required for the beauty treatments is reduced. Moreover, it is unnecessary to purchase plural facial treatment devices, one of which has one of the two functions and the other has the other function, and therefore it is very economical.

In this case, the facial treatment which alternately warms and cools the skin of the person 19 and the massaging by the vibrations are both executed simultaneously utilizing the Peltier element 12. However, the beauty treatment processes can be performed in combination with other beauty treatment techniques such as ultrasonic vibrations.

Further, when the facial treatment device having these various facial treatment functions is used, the facial treatment device can be constructed to arbitrarily select whether one of these beauty treatment processings is to be executed solely or a combination of these beauty treatment processings is to be executed.

In the facial treatment device according to the first embodiment, the eccentric weight 17 is attached to the vibrating motor 15 inside the body 10, and the probe 11 is vibrated by the drive of the motor 15. Therefore, the face of the person 19 can be alternately warmed and cooled, and the massages can be simultaneously given to the face of the person 19. Consequently, the beauty treatment effects such as the facial treatment and body slimming, and the relaxing effects can be synergistically obtained. Besides, the plural beauty treatment processes are executed together by one facial treatment device. Therefore, the processing time required for the beauty treatments can be reduced and the more economical facial treatments can be realized.

Embodiment 2

Figure 2:
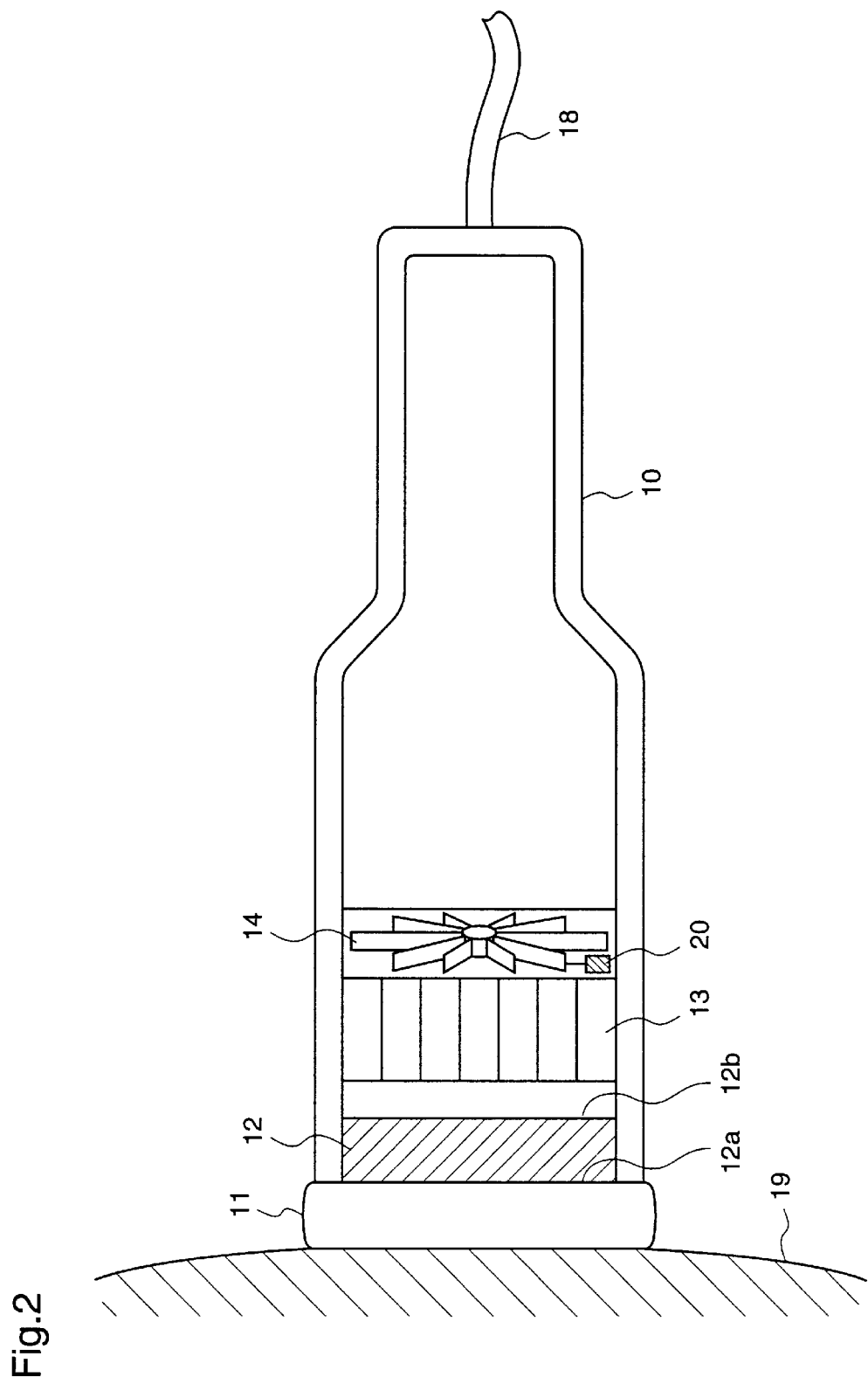
FIG. 2 is a diagram illustrating an example of a structure of a facial treatment device according to a second embodiment of the present invention.
Figure 3:
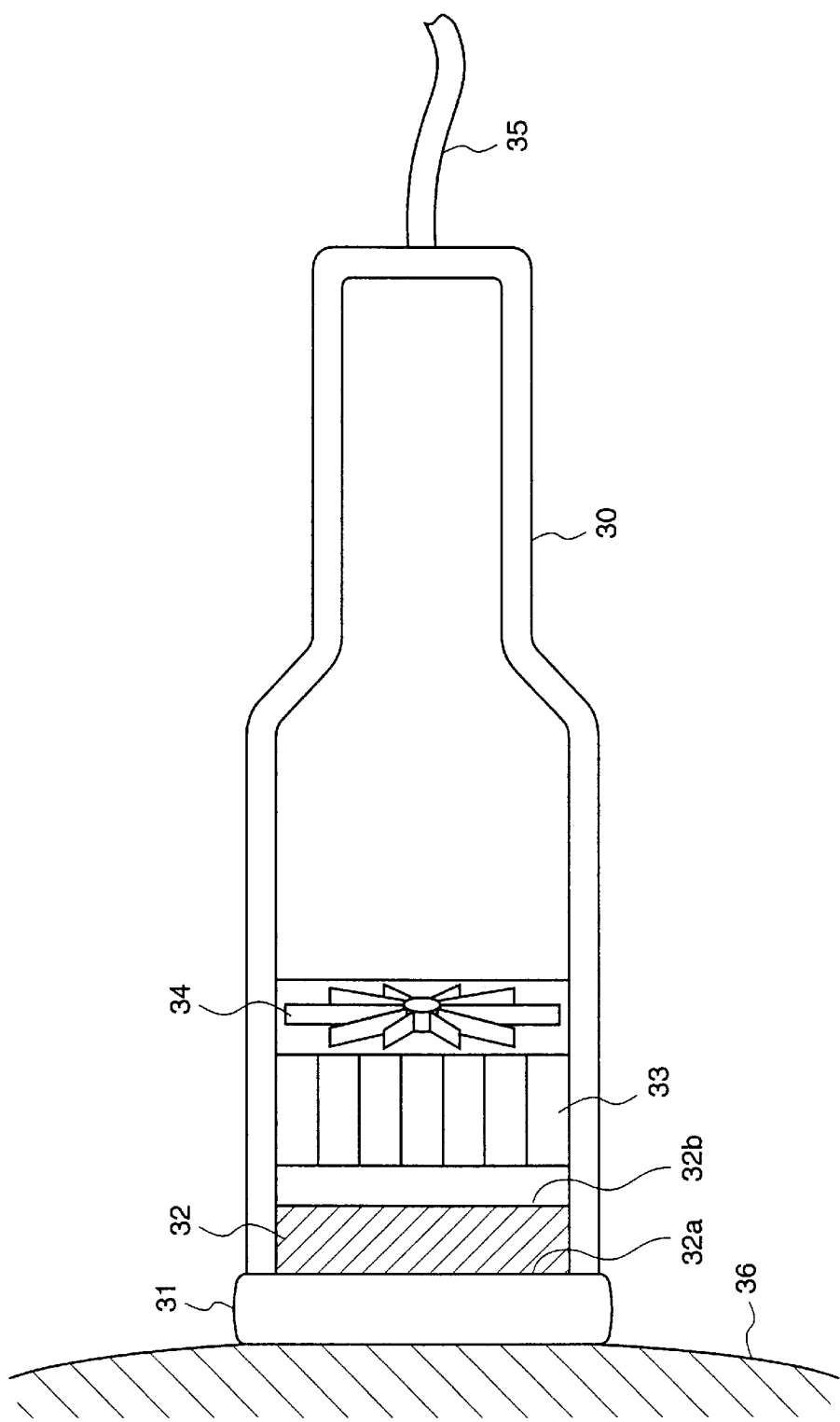
FIG. 3 is a diagram illustrating a structure of a prior art facial treatment device.
Figure 4:
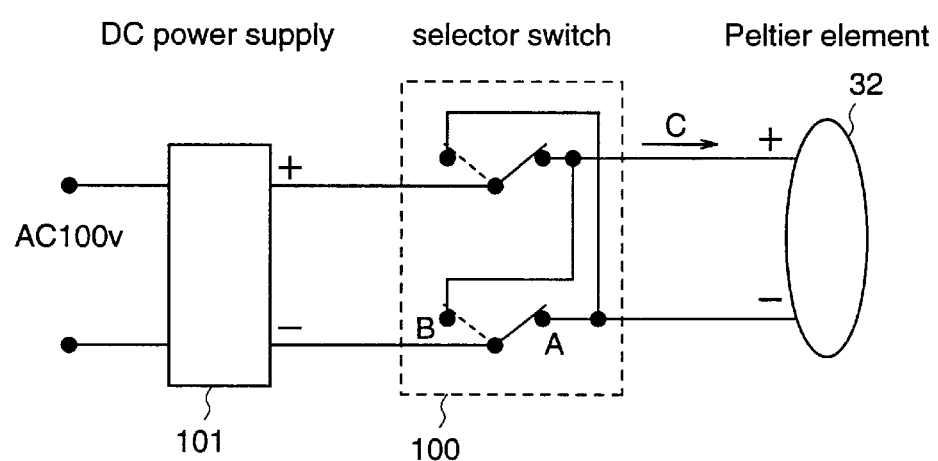
FIG. 4 is a diagram illustrating an example of a circuit which is connected to a Peltier element in the facial treatment device according to the prior art or the present invention.

FIG. 2 is a diagram illustrating a structure of a facial treatment device according to a second embodiment of the present invention. In the figure, the same reference numerals as those in FIG. 1 denote the same or corresponding parts. Common parts to those in the first embodiment are not described here.

In this second embodiment, an eccentric weight 20 is attached to a blade of the blower fan 14, instead of the vibrating motor in the body 10 provided in the first embodiment.

Accordingly, when the facial treatment device according to the second embodiment is used, the body 10 and the probe 11 are vibrated because of the turn of the blower fan 14 to which the eccentric weight 20 is attached. This vibration of the probe 11 gives comfortable stimuli to the face of the person 19, whereby the beauty treatment effects such as tightening of the skin, activation of the metabolism of the skin, removal of stains in pores, and the relaxing effects can be obtained together.

As described above, according to the facial treatment device of the second embodiment, the eccentric weight 20 is attached to a blade of the blower fan 14 for cooling the radiating fin 13 and the probe 11 is vibrated because of the turn of the blower fan 14. Therefore, the face of the person 19 is alternately warmed or cooled while the massage is simultaneously given to the person, whereby the beauty treatment effects such as facial treatment and body slimming and the relaxing effects can be obtained together. Besides, the plural beauty treatment effects are combined and executed by one facial treatment device. Therefore, the processing time required for the beauty treatments can be reduced and more economical facial treatments can be realized.

What is claimed is:

1. A facial treatment device, comprising:

a probe which has a high thermal conductivity and abuts a face of a person to be treated;

a Peltier element which is placed adjacent to the probe;

a radiating means which is placed adjacent to the Peltier element, for radiating heat which has been stored in the Peltier element;

a blower fan which is placed adjacent to the radiating means, for sending air and cooling the radiating means;

a vibration generating means which is placed adjacent to the blower fan, for vibrating the probe, said vibration generating means comprising a motor and a weight, the motor having a shaft, the weight being eccentrically directly attached to the shaft of the motor, the motor being driven to vibrate the probe;

a current supply means for supplying current to the Peltier element; and a current direction switching means for switching the direction of the current which is supplied by the current supply means to the Peltier element between forward and backward directions.

* * * * *

UNITED STATES PATENT AND TRADEMARK OFFICE
CERTIFICATE OF CORRECTION

PATENT NO. : 6,679,908 B2
DATED : January 20, 2004
INVENTOR(S) : Horohisa Shimizu It is certified that error appears in the above-identified patent and that said Letters Patent is hereby corrected as shown below:

Column 1,
Line 60, "nor" should read -- not --.
Line 65, "32b," should read -- 32b --.

Signed and Sealed this

Twenty-second Day of June, 2004

JON W. DUDAS
*Acting Director of the United States Patent and Trademark Office*